United States Patent [19]

Bruno

[11] 4,440,574

[45] Apr. 3, 1984

[54] NONSLUDGING COMPLEXES OF CHROMIUM AND STEARIC ACID

[75] Inventor: Salvatore A. Bruno, Wilmington, Del.

[73] Assignee: E. I. Du Pont de Nemours & Company, Wilmington, Del.

[21] Appl. No.: 468,770

[22] Filed: Feb. 22, 1983

[51] Int. Cl.³ ............................................... C09K 3/18
[52] U.S. Cl. ........................................ 106/2; 106/13; 106/287.18; 260/438.5 C
[58] Field of Search ...................... 106/2, 13, 287.18; 260/438.5 C

[56] References Cited

U.S. PATENT DOCUMENTS

| | | | |
|---|---|---|---|
| 2,256,161 | 8/1941 | Iler | 260/97 |
| 2,273,040 | 2/1942 | Iler | 91/68 |
| 2,424,803 | 10/1950 | Iler | 23/87 |
| 2,683,156 | 7/1954 | Iler | 260/438 |
| 3,284,215 | 11/1966 | Bartz | 106/13 |
| 3,287,141 | 11/1966 | Bartz | 106/13 |
| 3,907,576 | 9/1975 | Dear et al. | 106/2 |

*Primary Examiner*—Lorenzo B. Hayes

[57] ABSTRACT

A storage stable Werner complex of stearato, $CR^{+3}$, Cl and OH groups in the approximate molar ratio of 1:2:4:1 dissolved in from 15–30 weight percent pentanol and 47.7–32.7 weight percent isopropanol is disclosed. The solution contains from 5–7 weight percent chromium.

1 Claim, No Drawings

NONSLUDGING COMPLEXES OF CHROMIUM AND STEARIC ACID

BACKGROUND OF THE INVENTION

1. Field of the Invention

The present invention relates to storage stable Werner complexes of chromium and fatty acids, specifically stearic acid, in a mixed solvent system comprising isopropanol and n-pentanol.

2. Prior Art

U.S. Pat. No. 3,284,215 discloses Werner complexes of chromium and stearic acid which are prepared in a monohydric alcohol containing 1-4 carbon atoms.

SUMMARY OF THE INVENTION

The present invention relates to stearato chrome complexes dissolved in a mixture of isopropanol and n-pentanol which are storage stable. The complexes can be prepared from either polymeric basic chromic chloride hydrate or anhydrous basic chromic chloride and stearic acid.

DETAILED DESCRIPTION

Werner complexes of chromium and stearic acid have been prepared commercially in isopropanol for many years. The detrimental formation of a green insoluble sludge has always been a problem with some of these products.

Generally the products of this invention can be described as being a solution of water-soluble chromium complexes of the Werner type in which a trivalent chromium atom is coordinated with a stearato group in from 15–30 weight percent, as based on the total composition of n-pentanol and from 47.7–32.7 weight percent, based on the total composition, of isopropanol. The composition may also contain minor amounts of acetone. Generally the composition will contain from 5–7 weight percent complexed chromium. The Werner complex contains stearato, $Cr^{+3}$, Cl and OH groups in the approximate molar ratio of 1:2:4:1, respectively.

The complex solution can be prepared from either anhydrous monomeric basic chromic chloride or polymeric hydrated basic chromic chloride and stearic acid in a mixed solvent system containing isopropanol and n-pentanol.

The Werner complexes of the present invention fluid use in imparting water repellency to hydrophilic materials such as paper, leather and textiles.

EXAMPLES

Example 1 (Control)

Stearato Chrome Complex

Concentrated hydrochloric acid (5.5 g, 37.6%) is added to a mixture of 51.2 g of a polymeric basic chromic chloride hydrate of the formula $Cr_5OH_6Cl_9 \cdot 12H_2O$ and 37.6 g of stearic acid in 198 ml of isopropyl alcohol. The misture was warmed at 50° C. for 2 hours. The dark green solution was cooled to 20°–25° C. and filtered to remove a small quantity of insoluble material. This product yielded 222 g of a dark green solution of the stearato chrome complex.

Example 2

Stearato Chrome Complex

Concentrated hydrochloric acid (5.7 g, 36.3%) is added to a mixture of 51.1 g of a basic chromic chloride hydrate of the formula $Cr_5OH_6Cl_9 \cdot 12H_2O$ and 37.6 g of stearic acid in 150 ml of isopropyl alcohol and 50 ml of n-pentanol. The mixture is warmed at 50° C. for 2 hours. The dark green solution was cooled to 20°–25° C. and filtered to remove a small quantity of insoluble material. This procedure yielded a dark green solution of the stearato chrome complex, which on storage is stable toward the formulation of sludge.

Examples 3–8

Example 2 is repeated except the amounts of isopropanol and n-pentanol used were varied as reported in Table I. The percent solvent compositions reported in Table I are based on the total composition.

The samples from Examples 1–7 were stored at 55° C. for 10 days, followed by storage at 0°–5° C. for 2 days. The resulting samples were diluted with twice their volume of water and filtered. The filter cake was dried and the weight percent sludge determined and is reported in Table I.

TABLE I

| | Solvent Composition | | |
|---|---|---|---|
| Example | Isopropanol wt % | n-pentanol wt % | Sludge wt % |
| 1 | 62.2 | 0 | 4.8 |
| 2 | 46.6 | 16.1 | 0 |
| 3 | 0 | 63.1 | 2.7 |
| 4 | 30.9 | 32.0 | 0.1 |
| 5 | 38.7 | 24.1 | 0 |
| 6 | 51.3 | 11.3 | 1.1 |
| 7 | 54.5 | 8.1 | 1.7 |

Examples 9–13

Additional Werner complex samples are prepared from anyhydrous monomeric basic chromic chloride $Cr(OH)Cl_2$. The solutions contain approximately 5.7 weight percent Cr complexed in a mole ratio of stearato; Cr, Cl, OH of 1:2:4:1, the amount of n-pentanol reported in Table II and the remainder isopropanol. The accelerated sludge test was run by heating the samples under reflux for 5 hours. The samples were cooled, filtered and the percent residue (sludge) determined. The results are reported in Table II. Example 13 is a control in which isopropanol alone was used as the solvent.

TABLE II

| Example | n-pentanol wt % | Residue wt % |
|---|---|---|
| 9 | 22 | 0 |
| 10 | 15 | 0 |
| 11 | 10 | 0.31 |
| 12 | 5 | 0.60 |
| 13 | 0 | 0.73 |

I claim:

1. A solution comprising a Werner Complex of stearato, $Cr^{+3}$, Cl and OH groups present in the approximate ratio of 1:2:4:1, respectively, said solution containing from 5–7 weight percent chromium, from 15–30 weight percent n-pentanol and from 47.7–32.7 weight percent isopropanol.

* * * * *